(12) United States Patent
Vicalvi et al.

(10) Patent No.: US 10,463,988 B2
(45) Date of Patent: Nov. 5, 2019

(54) SINGLE USE SLURRYING AND CHROMATOGRAPHY SYSTEMS

(75) Inventors: John J. Vicalvi, Shrewsbury, MA (US); Joseph Makowiecki, Oxford, MA (US); Joseph D. Crowell, South Hamilton, MA (US); Parrish M. Galliher, Littleton, MA (US)

(73) Assignee: GE HEALTHCARE BIO-SCIENCES CORP., Marlborough, MA (US)

( * ) Notice: Subject to any disclaimer, the term of this patent is extended or adjusted under 35 U.S.C. 154(b) by 461 days.

(21) Appl. No.: 13/825,829

(22) PCT Filed: Sep. 23, 2011

(86) PCT No.: PCT/US2011/052975
§ 371 (c)(1),
(2), (4) Date: Apr. 1, 2013

(87) PCT Pub. No.: WO2012/040574
PCT Pub. Date: Mar. 29, 2012

(65) Prior Publication Data
US 2013/0186834 A1   Jul. 25, 2013

Related U.S. Application Data

(60) Provisional application No. 61/385,745, filed on Sep. 23, 2010.

(51) Int. Cl.
*B01D 15/22* (2006.01)
*G01N 30/56* (2006.01)
(Continued)

(52) U.S. Cl.
CPC .......... *B01D 15/22* (2013.01); *B01F 7/00141* (2013.01); *B01F 7/00858* (2013.01);
(Continued)

(58) Field of Classification Search
CPC ............ G01N 2030/565; G01N 30/56; G01N 30/6017; G01N 30/603; B01D 15/085;
(Continued)

(56) References Cited

U.S. PATENT DOCUMENTS 3,539,505 A * 11/1970 Stoeck et al. ................. 210/656
4,745,063 A    5/1988 Birschbach
(Continued)

FOREIGN PATENT DOCUMENTS

EP            1197474 A1 *  4/2002  ............... C02F 1/52
WO    WO 2003/101581      12/2003

OTHER PUBLICATIONS

Shriner, et al., "The Systematic Identification of Organic Compounds," (1980) John Wiley & Sons, Inc., 6th ed., 7 pages.*
(Continued)

*Primary Examiner* — Patrick J Orme
(74) *Attorney, Agent, or Firm* — Grogan, Tuccillo & Vanderleeden, LLP (57) ABSTRACT

Methods and systems for chromatography are disclosed that employ a flexible container configured to fit within a support structure and adapted to receive a filtration or absorptive medium, such as a chromatography resin. The flexible container can include at least one inlet, at least one outlet, and a separation barrier peripherally sealed within the container to separate the container into a resin containing portion and a drainage portion. The barrier can be configured to exclude the resin material from the drainage portion during use while allowing fluids to pass therethrough. The disposable chromatography system can further include one or more agitators disposed within the flexible container and adjustably configured to be raised or lowered in the flexible container. When the agitator is in the raised position, the resin packing material can operate in a settled, packed-bed
(Continued)

configuration. Alternatively, the agitator in the lowered position permits the chromatography resin packing material to operate in a mixed, slurry configuration.

23 Claims, 5 Drawing Sheets

(51) Int. Cl.
*B01F 7/00* (2006.01)
*B01F 7/16* (2006.01)
*B01F 13/02* (2006.01)
*B01F 15/00* (2006.01)
*B01F 7/22* (2006.01)
*B01F 13/06* (2006.01)
*B01F 13/08* (2006.01)
*G01N 30/50* (2006.01)
*G01N 30/60* (2006.01)
*B01F 15/06* (2006.01)

(52) U.S. Cl.
CPC ............... *B01F 7/161* (2013.01); *B01F 7/162* (2013.01); *B01F 7/1695* (2013.01); *B01F 7/22* (2013.01); *B01F 13/0211* (2013.01); *B01F 13/065* (2013.01); *B01F 13/0827* (2013.01); *B01F 15/0085* (2013.01); *G01N 30/56* (2013.01); *B01F 15/0022* (2013.01); *B01F 15/00162* (2013.01); *B01F 15/00175* (2013.01); *B01F 15/00227* (2013.01); *B01F 15/065* (2013.01); *G01N 30/50* (2013.01); *G01N 30/603* (2013.01); *G01N 30/6017* (2013.01); *G01N 2030/565* (2013.01)

(58) Field of Classification Search
CPC .... B01D 15/22; B01F 13/0211; B01F 13/065; B01F 13/0827; B01F 7/00141; B01F 7/00858; B01F 7/161; B01F 7/162; B01F 7/1695; B01F 7/22; B01F 7/1605; B01F 7/00625; B01F 7/00733; B01F 7/00633
USPC .......... 210/95, 143, 198.2; 422/70; 73/61.53
See application file for complete search history.

(56) References Cited

U.S. PATENT DOCUMENTS

| | | | |
|---|---|---|---|
| 5,423,982 A * | 6/1995 | Jungbauer et al. | 210/198.2 |
| 5,714,074 A | 2/1998 | Karlsson et al. | |
| 6,620,326 B1 * | 9/2003 | Lihme et al. | 210/635 |
| 7,306,734 B2 | 12/2007 | Ohnishi et al. | |
| 2002/0166816 A1 * | 11/2002 | Allen et al. | 210/656 |
| 2005/0242018 A1 * | 11/2005 | Hodgin et al. | 210/198.2 |
| 2005/0272146 A1 * | 12/2005 | Hodge et al. | 435/289.1 |
| 2006/0199260 A1 * | 9/2006 | Zhang et al. | 435/293.1 |
| 2008/0217248 A1 * | 9/2008 | Gebauer | B01D 15/206 |
| | | | 210/656 |
| 2009/0035856 A1 * | 2/2009 | Galliher et al. | 435/383 |
| 2010/0107752 A1 * | 5/2010 | Fernando | 73/149 |
| 2010/0170852 A1 | 7/2010 | Shu et al. | |

OTHER PUBLICATIONS

Office Action dated Jun. 13, 2014 Issued on Corresponding EP Application No. 11827607.0.
Search Report dated Mar. 24, 2014 Issued on Corresponding Chinese Patent Application No. 201180056029.6.

* cited by examiner

SINGLE USE SLURRYING AND CHROMATOGRAPHY SYSTEMS

CROSS-REFERENCE TO RELATED APPLICATIONS

This application is a filing under 35 U.S.C. 371 of international application number PCT/US2011/052975, filed Sep. 23, 2011, published on Mar. 29, 2012 as WO 2012/040574, which claims priority to United States provisional patent application number 61/385,745 filed Sep. 23, 2010.

FIELD OF INVENTION

The present invention relates generally to systems and methods for containing and manipulating liquids, suspensions and slurries, and in some embodiments specifically to filter aids, flocculants and liquid chromatography systems and methods.

BACKGROUND

In the process of removing particulates from bioreactor streams or conducting chromatography, a mixture of chemical substances may be resolved or separated by means of their selective retention as they are transported by a moving fluid or buffer solution through a slurry of particulates or particulates or resins packed in a chromatography column. A solution of the substances to be separated is referred to as the mobile phase of the system. The particulates or resin is known as the stationary phase and comprises finely divided particles which may be in the form of a gel or a solid, a micro or macroporous particle, fiber or fibrous material.

Typically, chromatography columns, referred to herein as simply a "column," comprise a hollow, vertically disposed non-cylindrical or cylindrical housing including, at the upper end, a liquid dispensing section through which the mobile phase is dispensed to the porous resin. A liquid collection section is typically located at the lower end of the column. The resin through which the mobile phase percolates is generally located between these two sections. Typically, the column is made from a rigid material, such as stainless steel, glass, or polyvinylchloride. The column is typically designed for multiple uses, requiring a cleaning process prior to each use, which can often be lengthy in duration and high in cost.

In the field of bio-manufacturing, there has been a well recognized need to optimize the contact time and area between the liquid and the resin. Techniques such as simulated moving bed chromatography have been developed along with packed-bed chromatography to most effectively perform the desired unit operation. Traditional columns may not allow for the easy conversion between slurried, or simulated moving bed chromatography, and packed-bed chromatography.

Similarly, the use of flocculants, fiber filter beds or filter aids that perform filtration to remove particulates from the mobile phase can require suspension in one mode of operations and repacking into a packed bed in another mode of operation.

Thus, a need exists for a new, single use or disposable system for adjusting particulate slurry or chromatographic operation, such as quickly switching between slurried and packed-bed operation and easily adjusting the height and volume of the bed or column.

Further, when filtration or chromatography is performed in a cleanroom environment, maintaining the desired low level of particulates in the ambient environment is often compromised by open tank operations and/or the need to thoroughly clean large vessels between batches. Restoring a cleanroom to a desired level, e.g., class 10000 or ISO 7, following a batch run can require lengthy air filtration cycles. Thus, there is a need to reduce the amount of cleaning needed in such systems so as to minimize the amount of time between batches.

SUMMARY OF THE INVENTION

Methods and disposable systems for chromatography, filtration, or absorption are disclosed that employ a flexible container configured to fit within a support structure and adapted to receive a filtration or absorptive medium, such as a chromatography resin packing material. The flexible container can include at least one inlet, at least one outlet, and a separation device comprising a manifold, mesh, membrane or frit filter peripherally sealed within the container to separate the container into a filter aid or resin containing portion and a drainage portion. The frit filter, mesh or membrane can be configured to exclude the filtration or absorptive medium from the drainage portion during use while allowing fluids to pass therethrough. The disposable system can include a nozzle device through which the mobile phase is pumped at high velocity to dislodge the packed bed and to aid in the slurrying of the filtration or absorptive media, filter aid or resin material. In the case of the chromatography system it can further include at least one agitator disposed within the bottom of the flexible container positioned above the separation device and an additional agitator mounted at the top of the flexible container adjustably configured to be raised or lowered in the flexible container. The upper agitator in the raised position can permit the filtration or absorptive medium to operate in a settled, packed-bed configuration. Alternatively, the agitator in the lowered position can permit the filter medium to operate in a mixed, slurry configuration.

The disposable chromatography system can further include at least one pump external to an in fluid communication to the flexible container for the purposes of pumping the mobile phase through the separation device and the flexible container. The system can further include a probe that can include a sensor coupled to the flexible container and can be operably connectable to a system controller. The at least one probe can include a temperature sensor, a pressure sensor, a UV sensor, a conductivity sensor, an optical density sensor, a pH sensor, and a turbidity sensor. The disposable chromatography system can have at least one sparger coupled to the flexible container and the sparger can be configured to deliver air to an interior of the flexible container 124, the sparger system being connected to inlet gas filters and outlet gas filters. The disposable chromatography system can further include a system controller operably coupled to at least one element of the flexible container, and the controller can be configured to control the external mobile phase pump and at least one parameter of operation of the chromatography system. The system can be a batch process system or an intermittent drain and fill system or a continuously operated slurry or resin contact system.

In another embodiment, a chromatography system can include a rigid support structure; and a flexible container configured to fit within a support structure and adapted to receive chromatography resin packing material. The flexible container can comprise at least one inlet, at least one outlet, and a separation device including but not limited to a manifold, fluid distribution device or frit filter peripherally sealed within the container to separate the container into a resin containing portion and a drainage portion. The separation device (ie frit filter, etc.) can be configured to exclude the resin material from the drainage portion during use while allowing fluids to pass therethrough. The separation device can optionally include at least one nozzle device through which the mobile phase is pumped at high velocity to dislodge the packed bed of filter aid or resin to aid in the suspension of the slurry. The rigid support structure can further include a translucent or transparent outer support vessel configured to allow visualization of an interior of the outer support structure 104. The rigid support structure can include an external motor drive system to operate the bottom mounted agitator and an actuator for adjusting the height of the top mounted or bottom mounted agitators disposed within the flexible container. The outer support structure can also be heated or cooled by being connected to a heating or cooling device. At least one agitator can be disposed within the flexible container, one located at the bottom of the flexible container positioned above the separation device and the other extending from the top of the flexible container which can be adjustably configured to be raised or lowered in the flexible container.

The disposable slurry and chromatography system can include at least one probe that can include a sensor coupled to the flexible container and operably connected to a system controller. The at least one probe can include a temperature sensor, a pressure sensor, a UV sensor, a conductivity sensor, an optical density sensor, a pH sensor, and a turbidity sensor. The disposable chromatography system can have at least one sparger coupled to the flexible container and the sparger can be configured to deliver air to an interior of the flexible container 124, the sparger system connected to at least one inlet gas filter and the outlet of the container connected to at least one exit gas filter. The disposable chromatography system can further include a system controller operably coupled to at least one element of the flexible container, and the controller can be configured to control at least one parameter of operation of the chromatography system as well as an external pump for pumping of the mobile phase through the separation device and the flexible container. The system can be a batch process system or an intermittent drain and fill system or a continuously operated slurrying device, resin contact or filtration system.

In another aspect of the invention, methods of performing chromatography (including filtration) can include the steps of placing a flexible container within a support structure, the flexible container having an integral separation device such as a manifold or a mesh or a frit element for retaining the filter medium, e.g., a slurried filter aid, fibrous material, flocculent or a chromatography resin packing material, loading the container with the filter aid or resin packing material via at least one inlet in the flexible container, filtering a liquid through the resin packing material by loading the liquid through at least one inlet and draining the liquid through at least one outlet in the flexible container, and releasing an eluate from the filter medium. The flexible container can further include separation device that includes at least one nozzle device through which the mobile phase is pumped at high velocity to dislodge the bed and aid in the suspension of the slurry. The flexible container can include at least one agitator mounted at the bottom above the separation device or at the top of the flexible container, and the method can further include lowering the top agitator into the container during use to engage the filter aid, flocculent or chromatography resin packing material and form a slurry thereof. The method can include raising the agitator within the container during use to operate the system in a packed-bed configuration. The method can further include disposing of the flexible container after use.

BRIEF DESCRIPTION OF THE DRAWINGS

The foregoing and other objects, features and advantages of the invention will be apparent from the following more particular description of illustrative embodiments of the invention, as illustrated in the accompanying drawings in which like reference characters refer to the same parts throughout the different views. The drawings are not necessarily to scale, emphasis instead being placed upon illustrating the principles of the invention. Those skilled in the art will understand that the devices and methods specifically described herein and illustrated in the accompanying drawings are non-limiting exemplary embodiments. The features illustrated or described in connection with one exemplary embodiment can be combined with the features of other embodiments. Such modifications and variations are intended to be included within the scope of the present invention.

DETAILED DESCRIPTION

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The term "chromatography" is used generally herein to encompass chromatography and particulate slurries used for filtration purposes. The disclosed system makes use of a filtration or absorption medium, which can include, without limitation, particulates, filter aids, fibrous or absorptive material, flocculating agents, activated membranes, or chromatography components. Generally stated, a chromatography system can include: (1) a means of pushing liquid through the system, (2) a means of separation of particles or molecules based on some physical or chemical property, 3) a means of detection, monitoring, and measurement of the post-separation stream and, optionally, (4) a means of heating or cooling the flexible container. Further details on chromatography systems can be found in International Patent Application Pub. No. WO2010/124159 by Xcellerex, Inc. published on Oct. 28, 2010 and herein incorporated in its entirety by reference.

In one embodiment of the invention, the system includes a disposable liner, or flexible container, that is placed within a rigid outer support structure, such as a rigid plastic, stainless steel or glass structure as well as a pump or other suitable means for pushing liquid through the slurry or chromatography system. The flexible container is adapted to contain a filtration medium, e.g., a porous matrix, such as a resin, or other adsorber; and a detector or sensor such as, for example, a UV detector. The chromatography column can be of any type, including a membrane absorber, fiber material or a monolith column.

The present invention generally provides systems and methods for performing liquid filtration, and in one embodiment, chromatography. By way of non-limiting example, the methods and devices allow for a disposable chromatography column and components. Disposable means that the component is designed to be discarded after use, and can be a single-use component, but can also include components that are designed to last more than a single-use. The disposable column can include a disposable liner, or flexible container, that is placed within a rigid outer support structure, such as a clear plastic, stainless steel with window portals or glass structure. The disposable system can also include disposable filter material housed within the disposable liner, a disposable agitation system, and disposable probes, such that the need to clean the system components prior to each use is minimized. Furthermore, the system components that contact product are entirely sealed to the ambient environment with no need to open the system after sterilization. The disposable components, such as the disposable liner, can be designed for use in a lower classification clean room than the standard class 10,000 clean room commonly required for traditional chromatography systems.

Figure 1:
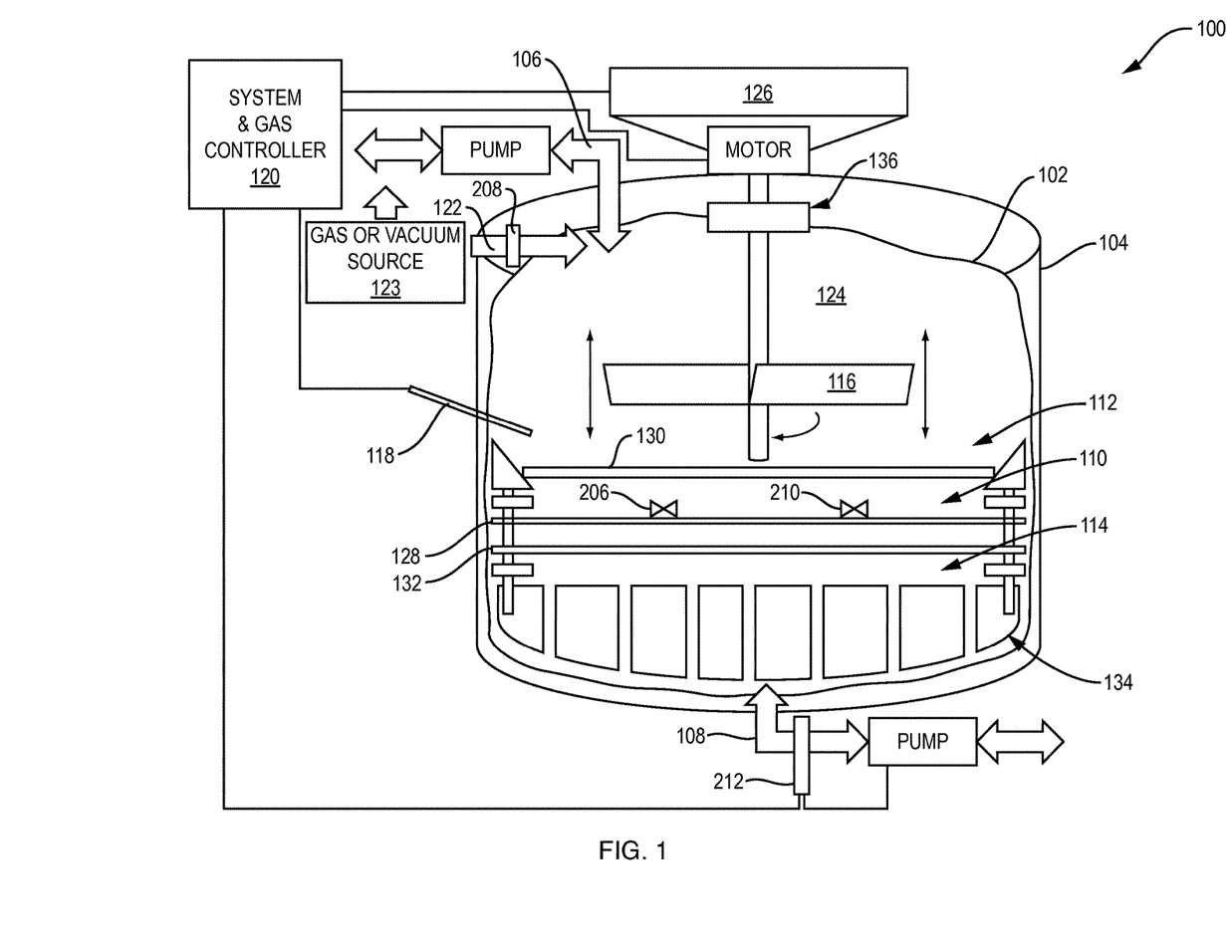
FIG. 1 is a schematic cross-sectional side view of a disposable chromatography system according to the invention.

FIG. 1 is a perspective view of an exemplary disposable chromatography system 100. The disposable chromatography system 100 includes a flexible container 102 and a support structure 104. The flexible container 102 can be configured to fit within the support structure 104. The flexible container 102 can have multiple inlet ports 106 and can have multiple outlet ports 108. The flexible container 102 can contain a separation device such as a manifold, mesh or frit filter 110 on the interior of the flexible container 124, and the frit filter 110 can be peripherally sealed so as to exclude material from one portion of the flexible liner from reaching another portion by passing between the flexible container 102 and the frit filter 110 along the periphery of the frit filter 110. The separation device can contain at least one nozzle device 206 for the passage of high velocity mobile phase pumped by the external pump which serves to dislodge the packed bed during the initial slurrying step to obtain a fully fluidized slurry, and at least one sparger 210.

The flexible container 102 can be produced from any flexible material that is non-reactive to pharmaceutical products, bio-molecules, and common chromatography solvents and buffers. For example, the flexible container can be constructed of Linear Low Density Polyethylene (LLDPE), Ethylene Vinyl Acetate (EVA), and Ultra-Low Density Polyethylene (ULDPE). The flexible container 102 can include a plastic bag chamber capable of containing welded ports from which to connect inlet and outlet tubing. The flexible container 102 can be configured to be disposable after a single use, or the flexible container 102 can be configured for repeated use in the disposable chromatography system 100. In an exemplary embodiment, the flexible container 102 is configured to fit within the support structure 104.

The support structure 104 can be configured to be translucent, or optically clear and transparent to visualize the flexible container 102 when the flexible container 102 is placed within the support structure 104. The support structure can be formed from any material capable of supporting the flexible container 102 and components when the system is in use. For example, the rigid support structure can be formed from a combination of 316 or 316L stainless steel members and transparent plastic members to allow a view of the interior of the support structure 104. The support structure 104 may also contain glass, 304 stainless steel, titanium, iron, or any other rigid material known to a person having ordinary skill to support the flexible container as disclosed. The support structure 104 can be jacketed for cooling or heating of the system 100.

The flexible container 102 can contain at least one input 106 and at least one outlet port or outlet 108. The at least one inlet 106 and outlet 108 should be integrally formed on the flexible container 102 so as to provide a closed system when the inlet and outlet ports 106, 108 are connected to the remainder of the system 100. Also, some filtration or chromatography applications require the introduction of gasses, liquids, and solids into the system, and can require the system to remain sealed to ambient gasses such as oxygen. Therefore, it is appreciated that the at least one inlet 106 and the at least one outlet 108 can be designed for the transport of gases, liquids, and solids. Outlet 108 can include a sensor 212. It is also appreciated that the at least one inlet 106 and the at least one outlet 108 for the outflow of gasses, liquids, and solids can be configured to allow flow both into and out of the flexible container 102 in instances where a reversal of flow is required for the system's operation. The system can further include one or more gas ports 122 and gas vent filter 208 in fluid communication with a gas or vacuum source 123 adapted to deliver or evacuate gases to or from the system.

The separation device (e.g., frit filter 110) can be configured to retain the filter medium in one portion of the flexible container. In an embodiment, the frit filter 110 can include a frit element 128, an upper frit retaining plate 130, and a frit screen 132. This embodiment allows for the easy reversal of liquid or gas flow within the system by retaining the frit material from the frit element 128 between the upper frit retaining element 130 and the frit screen 132. The frit material of the frit element 128 can be formed from traditional frit materials generally known to those skilled in the art of chromatography, such as porous film, porous membrane or porous plastic polymeric material, stainless steel, titanium, and Hastelloy Alloy C-22. The frit element 128 can contain a sparger 210. The frit filter 110 is supported underneath with a rigid distributor plate 134. The frit filter 110 can contain a nozzle device 206 through which high velocity mobile phase is pumped to dislodge the slurry and pores of various sizes and can be configured to allow liquids and gases to pass through freely while retaining solid materials in the resin containing portion 112 of the flexible container 102. In an embodiment, the frit filter 110 is configured to exclude resin material from the drainage portion 114 during use. The frit filter 110 can span the entire diameter of the flexible container 102 such that no resin can bypass the frit element 128. The frit filter 110 can be sealed along the periphery of the frit filter 110 to the flexible container 102 to protect against leakage from the resin containing portion 112 to the drainage portion 114 bypassing the frit material. The frit filter 110 can be sealed by known means such as fusing, hot or cold-welding, soldering, or integrally forming or mechanically clamping the upper frit retaining plate 130 and the frit screen 132 in the wall of the flexible container 102.

Figure 2:
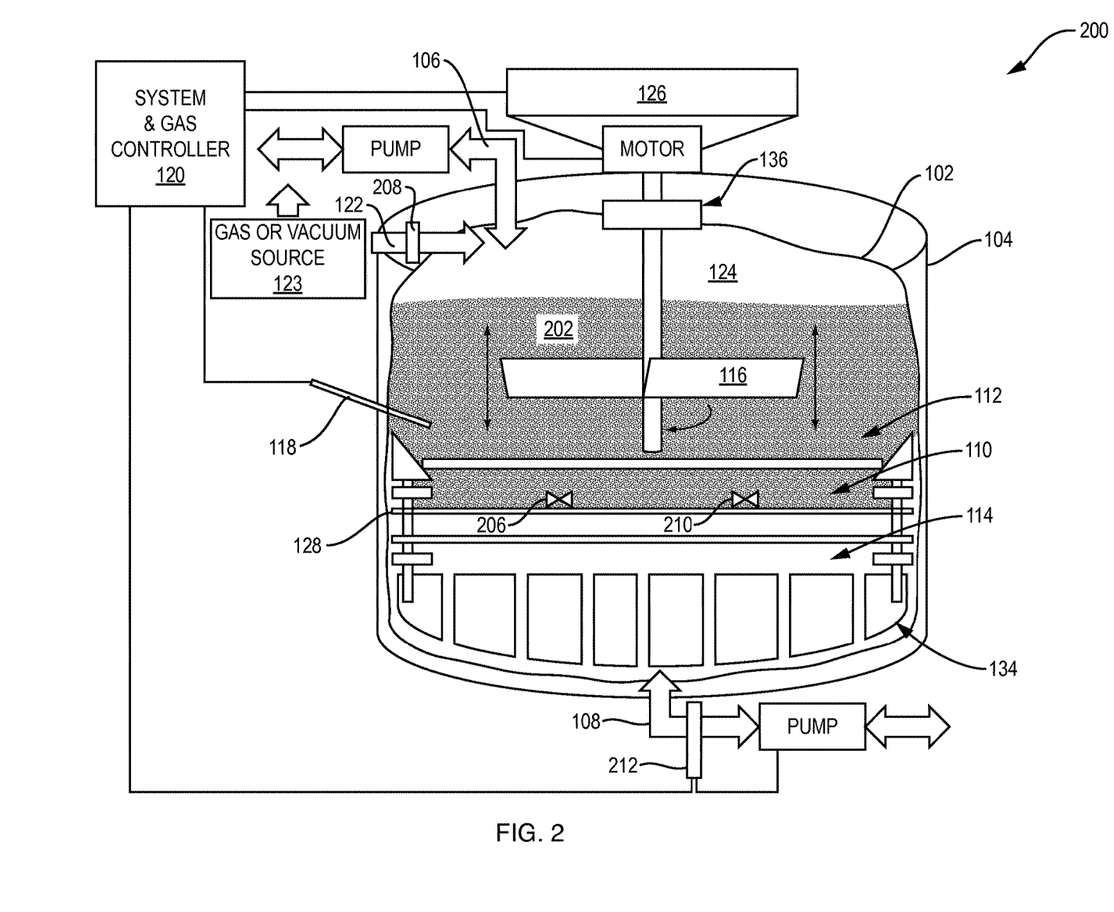
FIG. 2 is a schematic view of the system of FIG. 1 operating in a slurried bed mode.
Figure 3:
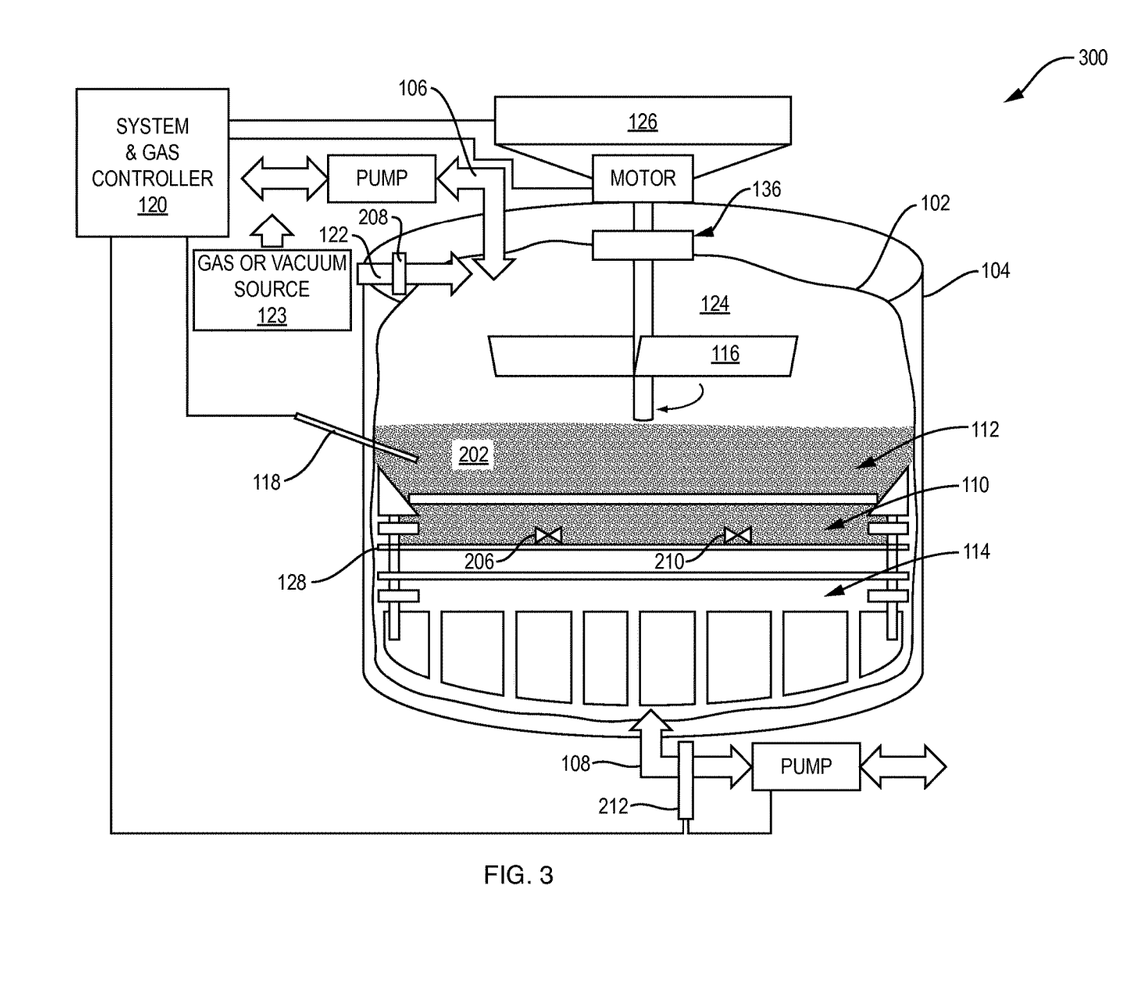
FIG. 3 is a schematic view of the system of FIG. 1 operating in a packed bed mode.

In an exemplary embodiment, an upper agitator 116 is disposed within the flexible container 102. As shown in FIGS. 1, 2, and 3, the agitator 116 can be configured to be raised or lowered within the flexible container 102 by an actuator 126 designed to adjust the height of the agitator 116. The agitator can be direct driven by a straight through shaft or magnetically driven by a magnetic drive mixer 136. The magnetic coupling of the magnetic drive mixer 136 can provide no penetration to the environment, which serves to reduce environmental contamination within the interior of the flexible container 124. The agitator 116 can be formed from any biocompatible material known to those skilled in the art of chromatography such as High Density Polyethylene (HDPE), 316L Stainless Steel, or titanium.

Figure 4:
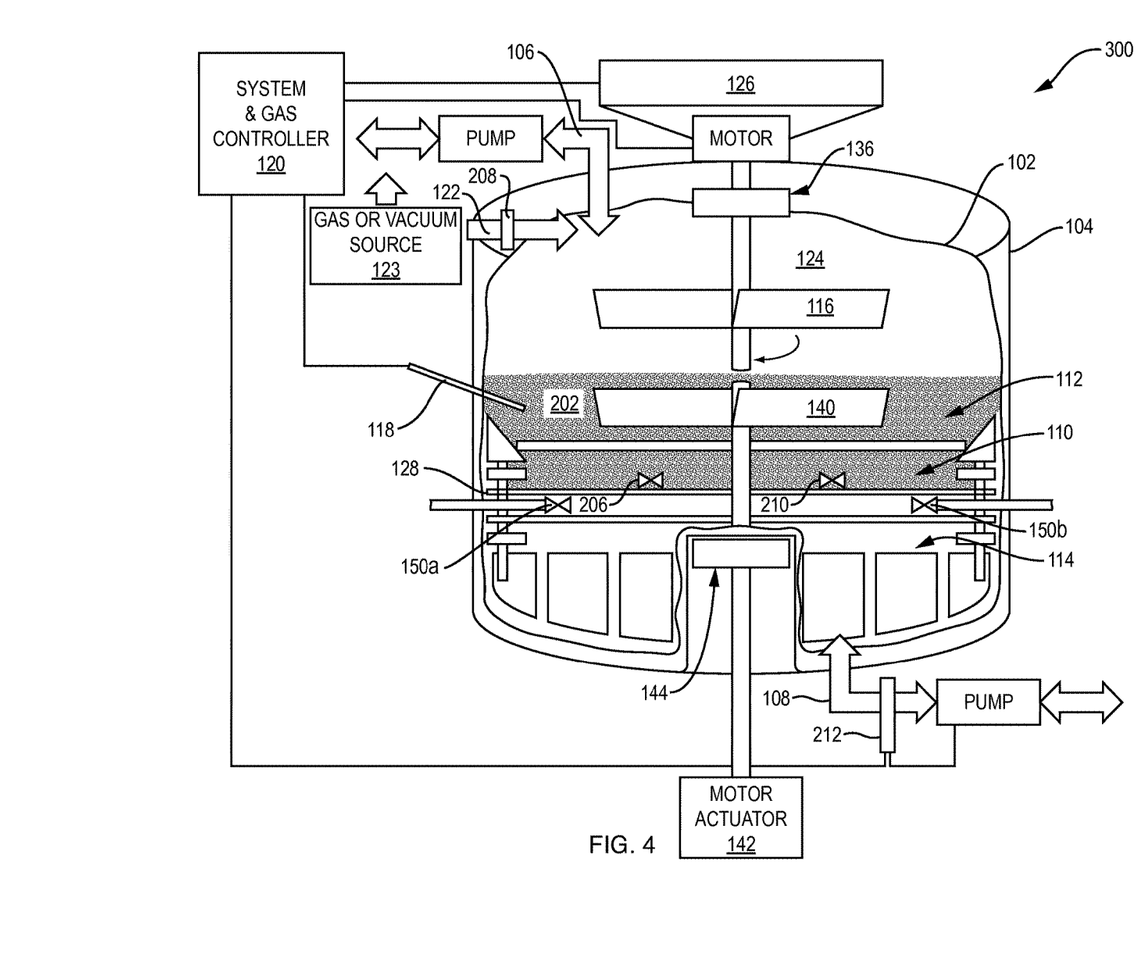
FIG. 4 is a schematic cross-sectional side view of another embodiment of a disposable chromatography system according to the invention.
Figure 5:
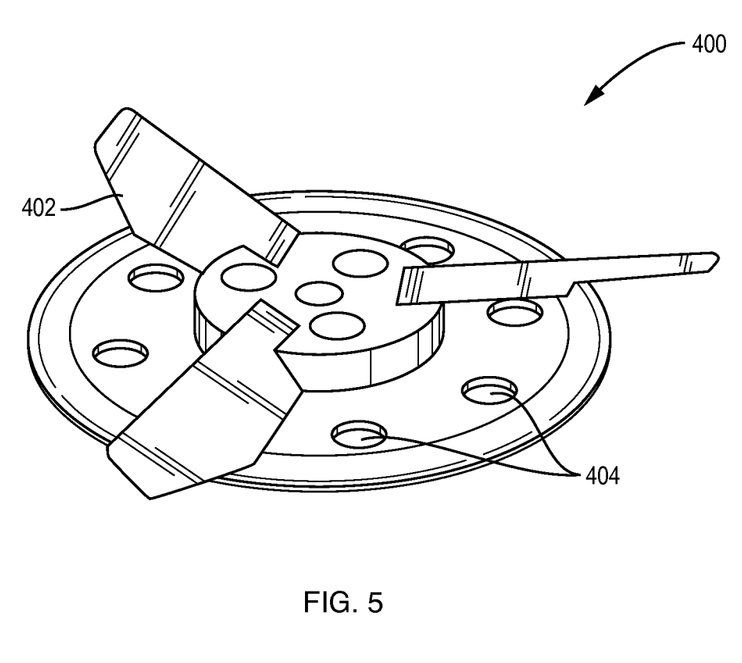
FIG. 5 is a perspective view of an agitator for use in the invention.

Similarly, as shown in FIG. 4, the system can also include a lower agitator 140, activated, for example, by a lower motor actuator 142 via a magnetic coupler 144. As shown in FIG. 4, the lower agitator is coupled magnetically to the lower agitator motor whose shaft is vertically disposed within a vertical tube that houses the lower agitator magnetic coupler. The agitator 140 can also include sparging discs 404, as shown in FIG. 5, and is disposed above the separation device. The frit element 128 can contain a sparger 210. Additionally, systems according to the present invention can include gas nozzles 150A, 150B to dislodge filter medium from the separation device, as shown in FIG. 4.

As is shown in FIG. 5, in one embodiment the agitator 400 includes impeller blades 402 that are at an angle to a sparging disc 404. The sparging disc 404 can be configured to introduce gas via an inlet/outlet gas filter to the flexible container 102. It is appreciated that any of the at least one inlet ports 106 and outlet ports 108 can be configured to introduce gas into the flexible container 102. Gas can be crucial to the functioning of the disposable chromatography system 100, 200, and 300 as a means to pressurized the flexible container to prevent the flexible container 102 from collapsing onto the agitator 116, as well as provide gasses that are essential to the success of the chromatography unit operation, for example by providing a nitrogen purge in the case of applications that are sensitive to oxygen. Furthermore, turbulent flow of gasses can provide a means to mix liquid and solid materials that are within the flexible container 102. A pressure sensor probe can provide feedback to a system controller 120 which is operably controlling the flow of gas into and out of the system 100. In the case of the gassed embodiment, the flexible filter is fitted with at least one outlet and one inlet gas filter.

As shown in FIGS. 1-4, the flexible container 102 can further include at least one probe 118 disposed within the flexible container 102. The probe 118 can include any sensor designed to monitor the system 100 known to those skilled in the art of chromatography. For example the probe 118 can include a temperature sensor, pressure sensor, ultraviolet sensor, conductivity sensor, pH sensor, and a turbidity sensor. The probes can be configured to give real time data to the system controller 120. It can be appreciated that any essential parameter of the system 100 can be monitored via a probe 118, such as whether the proper buffer has been delivered or whether the product is fully mixed throughout the resin or filter aid of fibrous material. The system controller 120 can be configured to operate the system 100 remotely via wireless connections, or via electronic connections known to those in the art. The system controller 120 can be configured to operate the agitator 116, the flow of material into and out of the flexible container via the at least one input and output ports 106, 108, the temperature of the system via the outer support structure 104. The system controller 120 can be configured to operate the actuator 126 mechanism that adjustably controls the height of the agitator 116.

As is shown in FIGS. 2 and 3, the system controller 120 can be configured to raise and lower the agitator 116 via the actuator 126. The system controller 120 can be configured to place the agitator 116 in a lowered position when the chromatography system is to be operated in a mixed, slurried configuration, as is shown in FIG. 2. Disposable chromatography system 200 illustrates the lowered configuration where agitator 116 is submerged in the chromatography resin packing material 202. This provides very efficient use of the chromatography resin packing material 202, since in a slurried mode all of the chromatography resin packing material 202 is employed at the same time. It can also be appreciated that depending on the stage of chromatography, such as loading or releasing the retentate, filtrate, or mobile phase, it can be advantageous to operate the chromatography system in different configurations, either packed-bed or slurried. FIG. 3 illustrates a packed-bed configuration where the system controller 120 has raised the agitator 116 above the chromatography resin packing material 202 and the lower agitator is turned off, allowing the chromatography resin packing material 202 to settle into a packed-bed configuration.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A disposable particulate slurry chromatography system, comprising:
    a flexible container configured to fit within a support structure and adapted to receive a particulate slurry filtration medium, the flexible container comprising:
    at least one inlet;
    at least one outlet;
    a separation barrier peripherally sealed within the container to separate the container into a filtration portion and a drainage portion, the separation barrier including a nozzle;
    a rigid distributor plate that supports the separation barrier; and
    wherein the separation barrier retains the filtration medium separately from the drainage portion during use while allowing fluids to pass therethrough, and the nozzle allows a high velocity mobile phase, pumped via an external pump, to fluidize the filtration medium via dislodging at least some of the filtration medium.

2. The system of claim 1, further comprising at least one agitator disposed within the flexible container and adjustably configured to be raised or lowered in the flexible container.

3. The system of claim 2, wherein the agitator in the raised position permits the filtration medium to operate in a settled, packed-bed configuration.

4. The system of claim 2, wherein the agitator in the lowered position permits the filtration medium to operate in a mixed, slurry configuration.

5. The system of claim 1, further comprising at least one probe comprising a sensor coupled to the flexible container and operably connectable to a system controller.

6. The system of claim 5, wherein the at least one probe can comprise a temperature sensor, a pressure sensor, a UV sensor, a conductivity sensor, an optical density sensor, a pH sensor, and a turbidity sensor.

7. The system of claim 1, wherein the separation barrier is a manifold or a mesh or a frit element and the filtration medium includes particulate beds, particulate slurries, filter aids, fibrous materials, flocculents, gels or chromatography resins.

8. The system of claim 1, further comprising at least one sparger coupled to the flexible container and configured to deliver air to an interior of the flexible container.

9. The system of claim 1, wherein the system further comprises a system controller operably coupled to at least one element of the flexible container, the system controller configured to control at least one parameter of operation of the system.

10. The system of claim 1, wherein the system is configured to be a batch process system, drain and fill intermittent system or a continuously operated perfusion system.

11. The chromatography system of claim 10, further comprising at least one sparger coupled to the flexible container and configured to deliver air to an interior of the flexible container.

12. A chromatography system, comprising:
a rigid support structure; and
a flexible container configured to fit within a support structure and adapted to receive chromatography resin packing material, the flexible container comprising:
at least one inlet;
at least one outlet;
a frit filter peripherally sealed within the flexible container to separate the container into a resin containing portion and a drainage portion, the frit filter including a nozzle;
a rigid distributor plate that supports the frit filter; and
wherein the frit filter retains the resin material separately from the drainage portion during use while allowing fluids to pass therethrough, and
the nozzle allows a high velocity mobile phase, pumped via an external pump, to fluidize the resin material via dislodging at least some of the resin material.

13. The chromatography system of claim 12, wherein the support structure is a transparent material configured to allow visualization of an interior of the outer support vessel.

14. The chromatography system of claim 13, wherein the support structure further comprises an actuator for adjusting the height of an agitator disposed within the flexible container.

15. The chromatography system of claim 14, further comprising at least one agitator disposed within the flexible container and adjustably configured to be raised or lowered in the flexible container.

16. The chromatography system of claim 15, further comprising at least one upper agitator and at least one lower agitator.

17. The chromatography system of claim 16, further comprising at least one probe comprising a sensor coupled to the flexible container and operably connected to a system controller.

18. A method of performing chromatography, comprising:
placing a flexible container within a support structure, the flexible container having an integral frit element and a rigid distributor plate that supports the frit element, the frit element includes a nozzle and is for retaining a chromatography medium;
loading the container with particulate slurry chromatography medium via at least one inlet in the flexible container;
filtering a liquid through the chromatography medium by loading the liquid through at least one inlet, fluidizing the chromatography medium by dislodging at least some of the chromatography medium via the nozzle through which the liquid is pumped at a high velocity via an external pump, and draining the liquid through at least one outlet in the flexible container; and
releasing an eluate from the chromatography medium.

19. The method of claim 18, wherein the flexible container further comprises an agitator, and the method further comprises lowering the agitator into the flexible container during use to engage the chromatography medium and form a slurry thereof.

20. The method of claim 18, wherein the flexible container further comprises an agitator, and the method further comprises raising the agitator within the container during use to operate the system in a packed-bed configuration.

21. The method of claim 18, wherein the flexible container further comprises at least one gas nozzle and the method further comprises delivering a gas to the frit element.

22. The method of claim 18, wherein the method further comprises disposing of the flexible container after use.

23. A disposable particulate slurry chromatography system, comprising:
a flexible container configured to fit within a support structure and adapted to receive a particulate slurry filtration medium, the flexible container comprising:
at least one inlet;
at least one outlet;
a separation barrier peripherally sealed within the container to separate the container into a filtration portion and a drainage portion, the separation barrier including a nozzle;
a rigid distributor plate that supports the separation barrier; and
wherein the separation barrier retains the filtration medium separately from the drainage portion during use of the chromatography system such that fluids are allowed to pass therethrough while the filtration medium remains a slurry, and
the nozzle allows a high velocity mobile phase, pumped via an external pump, to fluidize the filtration medium via dislodging at least some of the filtration medium.

\* \* \* \* \*